United States Patent
Mason

(10) Patent No.: US 8,182,429 B2
(45) Date of Patent: May 22, 2012

(54) ENHANCED FUNCTIONALITY AND ACCURACY FOR A WRIST-BASED MULTI-PARAMETER MONITOR

(75) Inventor: Martin K. Mason, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 365 days.

(21) Appl. No.: 12/094,221

(22) PCT Filed: Oct. 30, 2006

(86) PCT No.: PCT/IB2006/054017
§ 371 (c)(1),
(2), (4) Date: May 19, 2008

(87) PCT Pub. No.: WO2007/060560
PCT Pub. Date: May 31, 2007

(65) Prior Publication Data

US 2008/0306354 A1     Dec. 11, 2008

Related U.S. Application Data

(60) Provisional application No. 60/739,734, filed on Nov. 23, 2005.

(51) Int. Cl.
*A61B 5/02* (2006.01)
*A61B 5/04* (2006.01)

(52) U.S. Cl. ......... 600/485; 600/483; 600/513; 600/509

(58) Field of Classification Search .................. 600/485, 600/486, 490–503, 481, 483, 508, 509, 513
See application file for complete search history.

(56) References Cited

U.S. PATENT DOCUMENTS

| | | | |
|---|---|---|---|
| 4,779,626 A | | 10/1988 | Peel et al. |
| 4,854,323 A | * | 8/1989 | Rubin ........................... 600/382 |
| 4,896,676 A | * | 1/1990 | Sasaki .......................... 600/494 |
| 5,103,832 A | * | 4/1992 | Jackson ........................ 600/488 |
| 5,275,159 A | * | 1/1994 | Griebel ......................... 600/324 |
| 5,365,935 A | * | 11/1994 | Righter et al. ................ 600/523 |
| 5,406,952 A | * | 4/1995 | Barnes et al. ................. 600/485 |
| 5,691,478 A | | 11/1997 | Barry et al. |
| 6,251,080 B1 | * | 6/2001 | Henkin et al. ................ 600/490 |
| 7,215,991 B2 | * | 5/2007 | Besson et al. ................ 600/509 |
| 7,539,532 B2 | * | 5/2009 | Tran ............................. 600/509 |
| 7,539,533 B2 | * | 5/2009 | Tran ............................. 600/509 |

(Continued)

FOREIGN PATENT DOCUMENTS

EP     0465345 A1     1/1992

(Continued)

OTHER PUBLICATIONS

Weiss, M., Delta Press Indicator: A New Device for Adjustment and Monitoring Hemodynamic Pressure Transducer Position; 1999; The Internet Journal of Anesthesiology; 3(2)1-5.

(Continued)

*Primary Examiner* — Navin Natnithithadha

(57) ABSTRACT

A method for adjusting a blood pressure measurement to compensate for a pressure offset due to obtaining the blood pressure measurement at an elevation other than heart level is illustrated. The method includes measuring a blood pressure at a location above or below a heart level and adjusting the measured blood pressure in accordance with a pressure difference between the location at which the blood pressure is obtained and the heart level.

14 Claims, 4 Drawing Sheets

U.S. PATENT DOCUMENTS

| | | | |
|---|---|---|---|
| 7,558,622 B2* | 7/2009 | Tran | 600/509 |
| 2002/0095092 A1* | 7/2002 | Kondo et al. | 600/503 |
| 2004/0059230 A1* | 3/2004 | Thede et al. | 600/485 |
| 2004/0199081 A1 | 10/2004 | Freund et al. | |
| 2005/0075542 A1* | 4/2005 | Goldreich | 600/300 |
| 2005/0143671 A1* | 6/2005 | Hastings et al. | 600/513 |
| 2005/0148890 A1* | 7/2005 | Hastings | 600/509 |
| 2005/0197585 A1* | 9/2005 | Brockway et al. | 600/486 |
| 2005/0209526 A1* | 9/2005 | Ingley et al. | 600/529 |
| 2005/0215912 A1 | 9/2005 | Freund et al. | |
| 2007/0085690 A1* | 4/2007 | Tran | 340/573.1 |
| 2007/0100213 A1* | 5/2007 | Dossas et al. | 600/300 |
| 2008/0027679 A1* | 1/2008 | Shklarski | 702/182 |
| 2008/0051667 A1* | 2/2008 | Goldreich | 600/481 |
| 2008/0294058 A1* | 11/2008 | Shklarski | 600/502 |

FOREIGN PATENT DOCUMENTS

| | | |
|---|---|---|
| WO | 2004047633 A1 | 6/2004 |
| WO | 2006020917 A2 | 2/2006 |

OTHER PUBLICATIONS

Medwave, Inc.; Vasotrac Advertising Brochure—Vasotrac APM205A; 798-0037 Rev. C.

Medwave, Inc.; Vasotrac Technical Information for Vasotrac 205A; 798-0029 Rev. C—MDWV72003-20,000.

Medwave, Inc.; Brochure—Technical Information for Vasotrac DS APM205A; 798-0133 Rev. B—MDWV102004-3000.

* cited by examiner

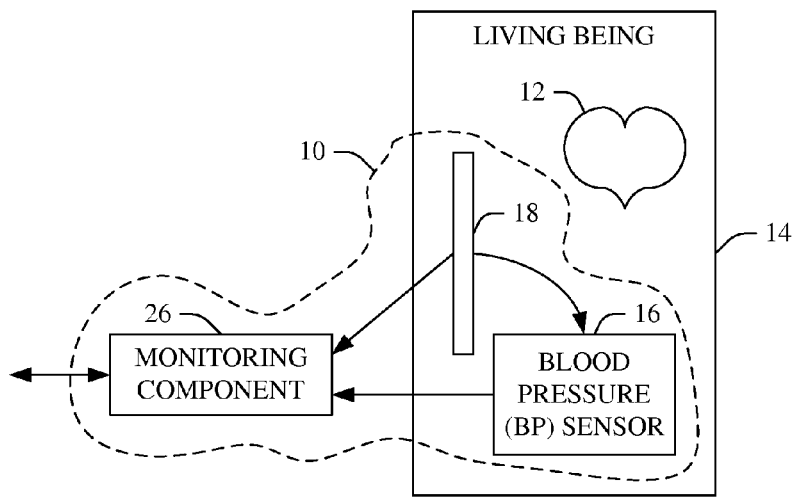
FIGURE 1
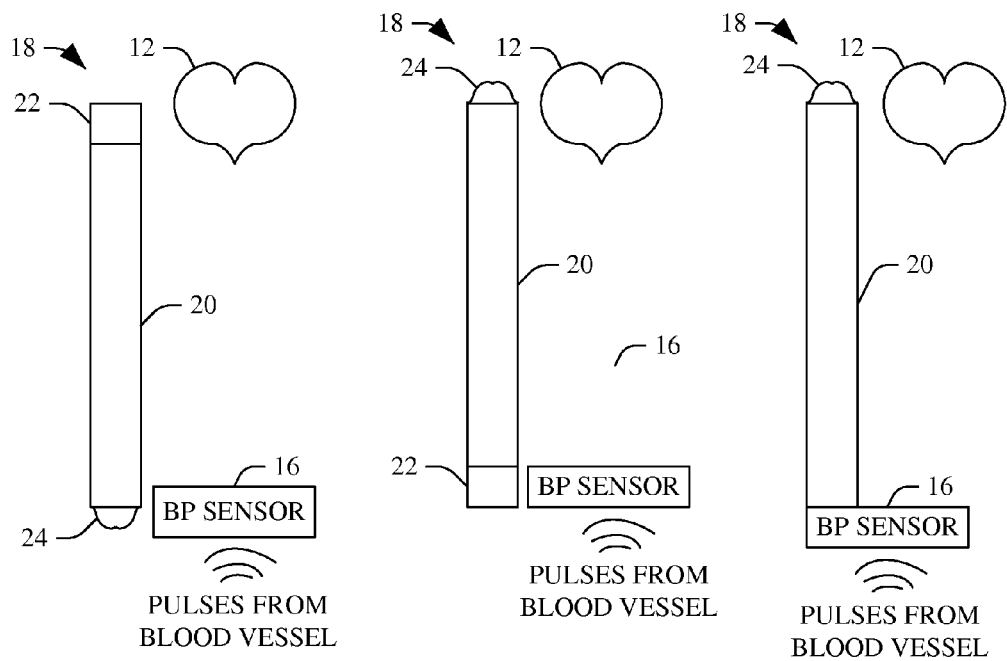
FIGURE 2
FIGURE 3
FIGURE 4

ENHANCED FUNCTIONALITY AND ACCURACY FOR A WRIST-BASED MULTI-PARAMETER MONITOR

CROSS REFERENCE TO RELATED APPLICATIONS

This application is a 371 of PCT/IB2006/054017, filed Oct. 30, 2006, which claims the benefit of U.S. provisional application Ser. No. 60/739,734 filed Nov. 23, 2005, which is incorporated herein by reference.

The following relates to patient monitoring systems. It finds particular application to blood pressure monitoring, and, more particularly, to adjusting blood pressure measurements obtained at locations above and below heart level in order to compensate for hydrostatic pressure differences.

Patients are commonly connected to a plurality of patient monitoring devices that measure physiological parameters such as blood pressure (invasive and non-invasive), Oxygen saturation (SpO2), temperature, heart electrical activity (ECG), etc. These parameters are measured either continuously, for example, via a bedside monitor, or intermittently, for example, during a "spot check" by a clinician.

Clinicians usually prefer measuring blood pressure at heart level, or central arterial. When blood pressure is acquired at locations not level (e.g., above or below) with the heart, an inaccuracy is introduced into the measurement. This typically results in a less accurate or sometimes incorrect blood pressure reading. By way of example, a wrist-mounted blood pressure measurement device may be above or below the patient's heart, depending on the location of the hand/arm of the patient. When it is above or below heart level, an offset due to a hydrostatic pressure difference attributable to the difference in height of the blood pressure measurement device relative to the heart is introduced into the blood pressure measurement. Changes in arm altitude may result in a pressure reading change that could be interpreted as a significant physiological change.

One solution is to have the patient position (raise or lower) their arm or other appendage supporting the blood pressure measurement device to heart level when measuring blood pressure. However, this may not always be practical, for instance, where the patient cannot (e.g., due to paralysis) or should not (e.g., due to a broken bone) move the appendage. In addition, the periodicity of the measurements may require the patient to perform such movements one or more times every hour, which may prevent the patient from sleeping or lying in a position other than supine.

In one embodiment, a method for adjusting a blood pressure measurement to compensate for a pressure offset due to obtaining the blood pressure measurement at an elevation other than heart level is illustrated. The method includes measuring a blood pressure at a location above or below a heart level and adjusting the measured blood pressure in accordance with a pressure difference between the location at which the blood pressure is obtained and the heart level.

One advantage includes adjusting a blood pressure measurement to compensate for pressure differences between the location where the blood pressure is obtained and the level of the heart.

Another advantage resides in hydraulically correcting a blood pressure obtained at a height above or below the heart.

Another advantage lies in reading physiological parameters from an individual through a single multi-parameter monitoring device.

Still further advantages will become apparent to those of ordinary skill in the art upon reading and understanding the detailed description of the preferred embodiments.

The drawings are only exemplary of selected embodiments and are not to be taken as limiting the invention.

FIG. 1 illustrates a blood pressure measurement compensation system.

FIG. 2 illustrates a first embodiment of an offset pressure measuring device of the blood pressure measurement compensation system.

FIG. 3 illustrates another embodiment of the offset pressure measuring device of the blood pressure measurement compensation system.

FIG. 4 illustrates yet another embodiment of the offset pressure measuring device of the blood pressure measurement compensation system.

Figure 6:
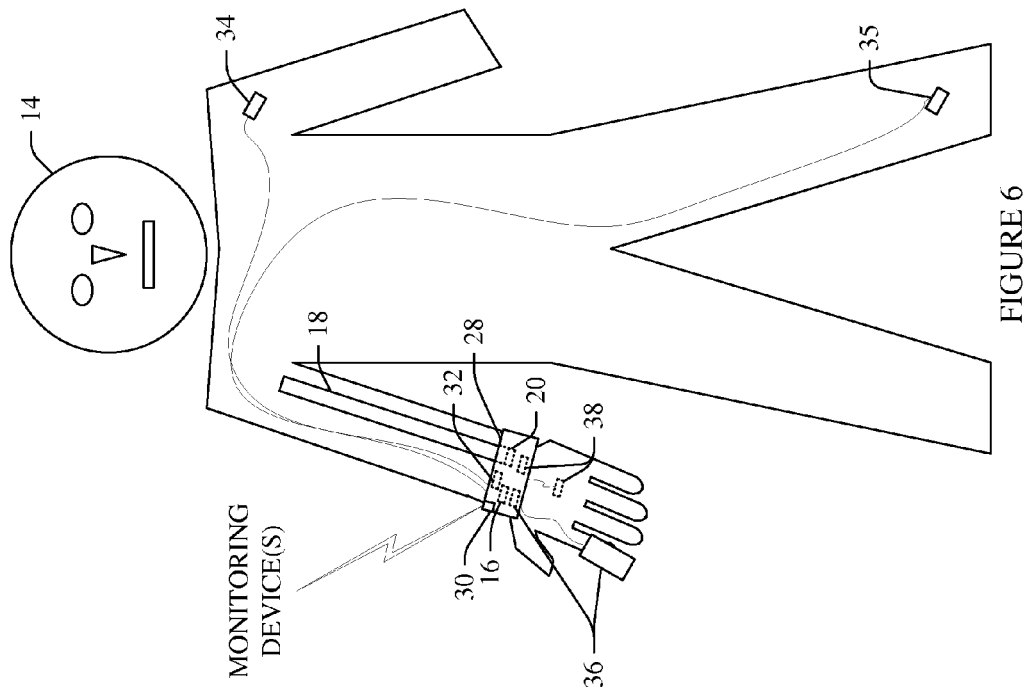
FIG. 6 illustrates an example of the offset pressure measuring device used with a wrist-based monitoring device facilitates measuring multiple physiological parameters.

FIG. 1 illustrates a blood pressure measurement compensation system ("system") 10 for adjusting blood pressure measurements acquired at locations above and below a central arterial level of a heart 12 of a living being (e.g., a human, an animal, etc.) 14 by concurrently measuring a hydrostatic offset and blood pressure and combining (e.g., adding, subtracting, etc.) the offset with the blood pressure to generate an offset-adjusted blood pressure.

The system 10 includes a blood pressure (BP) sensor 16 that senses a blood pressure (e.g., a pressure exerted by the blood on the walls of the blood vessels) in the living being 14. The blood pressure sensor 16 can be formed from quartz, silicon, or the like, and includes one or more components such as, for example, piezoelectric, resistive, solid state, etc. transducers, amplifiers, signal converters (e.g., analog to digital), filters, etc. Typically, the blood pressure sensor 16 is used to measure arterial blood pressure (e.g., in the large arteries such as the brachial artery in the arm). However, it can also be used to measure venous blood pressure. Pressure measurements may be invasive using an arterial or venous catheter. Alternatively the arterial pressure may be obtained non-invasively using a compression cuff or similar external device to detect arterial pressure. These measurements are typically processed with one of several well established algorithms (such as the oscillometric method) to obtain various blood pressure parameters. As depicted, the non-invasive blood pressure sensor 16 is arbitrarily placed in contact with a region of the living being 14. The particular region depends on a type of the blood pressure sensor 16 (e.g., a wrist based sensor is placed on the wrist, an ear based sensor is placed in the ear, an arm based sensor is placed on the arm, etc.) as well as other factors such as a condition of the patient, the particular circumstances, etc.

The system 10 further includes an offset pressure measuring device 18, which measures the offset pressure difference (about 22.4 mmHg per foot of altitude) between a height of the blood pressure sensor 16 and the heart 12. The size (e.g., length, width, height, diameter, etc.) of the offset pressure measuring device 18 can be arbitrarily determined based on age, gender, etc. of the living being 14 and/or the appendage used to measure blood pressure. For instance, when designing the offset pressure measuring device 18 for measuring the blood pressure of an adult human male at the wrist, the offset pressure measuring device 18 can be designed to extend from about the upper arm level to about the wrist level (plus a margin to accommodate non-average individuals) of an average size adult human.

In a preferred embodiment illustrated in FIG. 2, the offset pressure measuring device 18 includes a flexible cavity 20 (e.g., a tube) filled with a fluid that has a density similar to blood (e.g., water, silicon oil, etc.) or with a known relationship to the density of blood. Minimizing the diameter of the tube minimizes the weight of the tubular cavity. A pressure sensor 22 is disposed at an end that is positioned to remain at about heart level. An expansion device 24 such as an elastomeric reservoir that allows for expansion and contraction of the fluid is disposed at an opposing end of the fluid filled cavity 20, which is positioned proximate the blood pressure sensor 16. Alternatively, the elastomeric reservoir 24 can be disposed at the end positioned to remain at about heart level and the pressure sensor 22 can be disposed at the opposing end near the blood pressure sensor 16 as illustrated in FIG. 3. The relative positioning (near the heart 12 or near the blood pressure sensor 16) of the pressure sensor 22 affects the sign (negative or positive) of the offset pressure.

Similar to the blood pressure sensor 16, the cavity pressure sensor 22 can be formed from quartz, silicon, etc., and includes components such as piezoelectric, resistive, solid state, etc. transducers, amplifiers, signal converters (e.g., analog to digital), filters, etc.

A surface of the elastomeric reservoir 24 is adjacent to the fluid within the fluid filled cavity 20 and an opposing surface of the elastomeric reservoir 24 is adjacent to the environment. The elastomeric reservoir 24 is designed to expand and contract in order to dynamically compensate for factors such as temperature, atmospheric pressure, bending of the cavity 20, etc to ensure that the surface of the fluid in contact with the reservoir 24 remains at atmospheric pressure.

The offset pressure measuring device 18 measures a pressure of the fluid within the fluid filled cavity 20 relative to atmospheric pressure. Likewise, the blood pressure sensor 16 measures the blood pressure of the living being 14 relative to atmospheric pressure.

Returning to FIG. 1, the measured blood and offset pressures are conveyed to the monitoring component 26, which uses the offset pressure (e.g., adds, subtracts, etc.) to correct the blood pressure measurement. It is to be appreciated that the offset pressure can be about zero, for instance, when the blood pressure sensor 16 is at about heart level. Thus, the correction may be from substantial to negligible.

In one example, the blood pressure sensor 16 and the offset pressure measuring device 18 independently convey their respective measured pressures to a monitoring component 26. In another instance, the blood pressure measurement and the offset pressure measurement are conveyed through a common channel to the monitoring component 26. For example, the blood pressure measurement and the offset pressure measurement can be combined into a single signal and/or routed through a common cable to the monitoring component 26. As another example, the blood and offset pressures are analog or digitally combined before the monitoring component.

FIG. 4 illustrates an alternative embodiment in which the fluid filled cavity 20 is operatively coupled to the blood pressure sensor 16 instead of the cavity pressure sensor 22. In this configuration, the offset pressure is hydraulically combined with the blood pressure to correct for any differences in the height of the blood pressure sensor 16 with respect to the heart 18. More specifically, the blood pressure is typically measured across a diaphragm relative to atmosphere, as is the pressure in the cavity. By connecting the fluid in the tubular cavity with the diaphragm, the blood pressure can be measured relative to the offset pressure. The offset-adjusted blood pressure is measured by the blood pressure sensor 16 and conveyed to the monitoring component 26.

Returning to FIG. 1, the monitoring component 26 can be software and/or hardware. In addition, it can be a stand alone component and/or integrated with a bedside monitor, a wrist-based multi-parameter monitoring device, a central monitoring station, a computer, a personal data assistant (PDA), a portable monitor, etc. The monitoring component 26 can communicate via wire and/or wirelessly technologies with the blood pressure sensor 16, the offset pressure sensor 18 and/or components associated therewith, and other devices such as, for example, a bedside monitor, a portable monitor, a central monitoring station, a computer, a personal data assistant (PDA), a network, etc.

In connection with the exemplary embodiments described in FIGS. 2 and 3, the monitoring component 26 can serially and/or concurrently receive the measured blood pressure and offset pressure and combine the measurements in the analog and/or digital domains. The monitoring component 26 can also process the individual and/or combined signals. Examples of suitable processing include conditioning, filtering, amplifying, etc. Likewise, the monitoring component 26 can process the offset-adjusted blood pressure measurement obtained from the embodiment described in FIG. 4.

Figure 5:
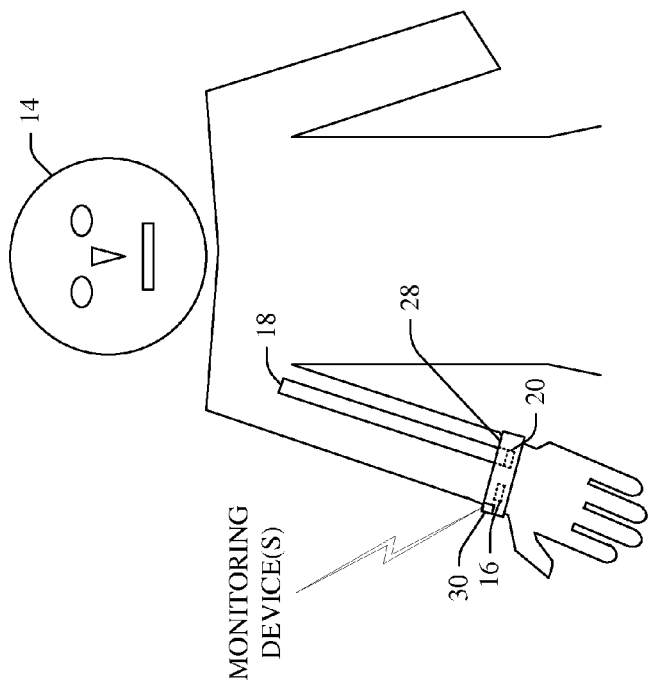
FIG. 5 illustrates an example of the offset pressure measuring device used with a measure blood pressure measuring wrist-based monitoring device.

FIG. 5 illustrates an example of the offset pressure measuring device 18 used with a wrist-based monitoring device 28 that has at least a capability to measure a blood pressure at the wrist. The wrist-based monitoring device 28 can be variously shaped to attach around at least a portion of a wrist. For instance, the wrist-based monitoring device 28 can be shaped similar to a wrist band or bracelet and placed around the wrist. In addition, the wrist-based monitoring device 28 can be affixed through snaps, laces, elastic, Velcro, tape, a clamp, etc.

The wrist-based monitoring device 28 includes the blood pressure sensor 16. In a preferred embodiment, the blood pressure sensor 16 employs a tonometric or oscillometric non-invasive blood pressure (NIBP) approach in which the blood pressure is measured in the radial artery. With this technique, the blood pressure sensor 16 includes a small fluid filled chamber that is positioned over the artery on the wrist. The chamber is pressed down on the skin by a weight, an inflatable cuff, an electromotive force (e.g., via a motor), etc. until a suitable (e.g., predetermined, maximum, etc.) dynamic pressure signal is detected. Thereafter, systolic, diastolic, and continuous BP measurements can be obtained.

While measuring blood pressure via the blood pressure sensor 16, the offset pressure measuring device 18 measures the offset pressure attributable to the difference in height between the offset pressure sensor 20 and the heart. As depicted, the offset pressure sensor 20 is positioned at about the level of the blood pressure sensor 16 such that the offset pressure measurement measures the pressure difference resulting from the difference in height between the blood pressure sensor 16 and the heart. As described above, there are multiple exemplary configurations for the offset pressure measuring device 18. This example illustrates the configuration described in FIG. 3. It is to be understood that this configuration is illustrated for explanatory purposes and is not limiting. The configurations described in FIGS. 2 and 4 as well as other configurations (not shown) and derivations thereof are contemplated herein.

The measured blood pressure and offset pressure (or offset-adjusted pressure) is conveyed by a transceiver 30 of the wrist-based monitoring device 28 to one or more monitoring devices. The signals may be processed by the transceiver 30 (e.g., digitized, filtered, analyzed, etc.) or they may be sent to the monitor in their original analog form. With separate blood pressure and offset pressure measurements, the signals can be serially and/or concurrently (e.g., in parallel or combined) conveyed by the transceiver sensor 30 to the monitoring device(s). The transceiver 30 can transfer the signals via wire (e.g., analog cable, Ethernet, Universal Serial Bus, serial and/or parallel communication ports, modem, Firewire, etc.) and/or wireless (e.g., radio frequency (RF), infrared (IR), optical, etc.) technologies. Suitable physical mediums include, but are not limited to, category 1-5 shielded or unshielded twisted pair cable, coaxial cable, etc.

FIG. 6 illustrates an example of the offset pressure measuring device 18 used with a wrist-based monitoring device 28 that includes facilitates for measuring one or more of the following: blood pressure, heart electrical activity (ECG), blood oxygen (Sp02), and skin temperature. As described in connection with FIG. 5, the wrist-based monitoring device 28 includes the blood pressure sensor 16 for measuring blood pressure at the wrist. In this example, the offset pressure sensor 20 is located at an end of the offset pressure measuring device 18 that is positioned near the blood pressure sensor 16 within the wrist-based monitoring device 28. However, the configurations described in FIGS. 1 and 4 can also be used. The blood pressure sensor 16 and the offset pressure sensor 20 respectively measure a blood pressure and an offset pressure as described above, and these measurements are conveyed to one or more monitoring devices via the transceiver 30.

The wrist-based monitoring device 28 also includes a heart electrical activity sensor 32 that is used with at least one other heart electrical activity sensor 34 to acquire heart electrical signals for generating an electrical activity map of the heart. Additional sensors 35 may be used to obtain alternate ECG leads. For instance, signals obtained by the electrical activity sensors 32, 34, and 35 can be used to generate a three or more lead ECG. The electrical activity sensors 34 and/or 35 can convey signals via wire and/or wireless technologies to the wrist-based monitoring device 28, and subsequently conveyed along with the signal from the electrical activity sensor 32, via the transceiver 30, to the monitoring device(s). It is to be appreciated that the electrical heart signals can be serially and/or concurrently conveyed with the blood pressure and offset pressure (or offset-adjusted blood pressure) measurements. In another embodiment (not shown), the wrist-based monitoring device 28 does not utilize the electrical activity sensor 32, but instead receives electrical heart signals from three or more electrical activity sensors 34 suitably placed on the living being 14, and is used as a conduit to convey the signals to the monitoring device(s) through the transceiver 30.

The wrist-based monitoring device 28 is also coupled to a blood oxygen sensor 36 that continuously and/or an intermittently measures blood oxygen. As depicted, the blood oxygen sensor 36 can be integrated within the wrist-based monitoring device 28 or coupled thereto through wire and/or wireless technology. In one instance, an integrated blood oxygen sensor 36 includes a reflective sensor that interrogates the inner wrist. The blood oxygen measurement is serially and/or concurrently conveyed with other physiological measurements (e.g., blood pressure, offset pressure, offset-adjusted blood pressure, heart electrical activity, etc.) to the monitoring device(s) via the transceiver 30. An external blood oxygen sensor 36 can be part of a finger cuff, ear probe, or other device.

The wrist-based monitoring device 28 optionally includes a temperature sensor 38, which preferably is thermistor or the like positioned adjacent to the skin to measure a temperature at skin surface. As depicted, the blood oxygen sensor 36 can be integrated within the wrist-based monitoring device 28 or coupled thereto through wire and/or wireless technology. The temperature measurement is serially and/or concurrently conveyed with other physiological measurements (e.g., blood pressure, offset pressure, offset-adjusted blood pressure, heart electrical activity, blood oxygen, etc.) to the monitoring device(s) via the transceiver 30 to the monitoring device(s).

Figure 7:
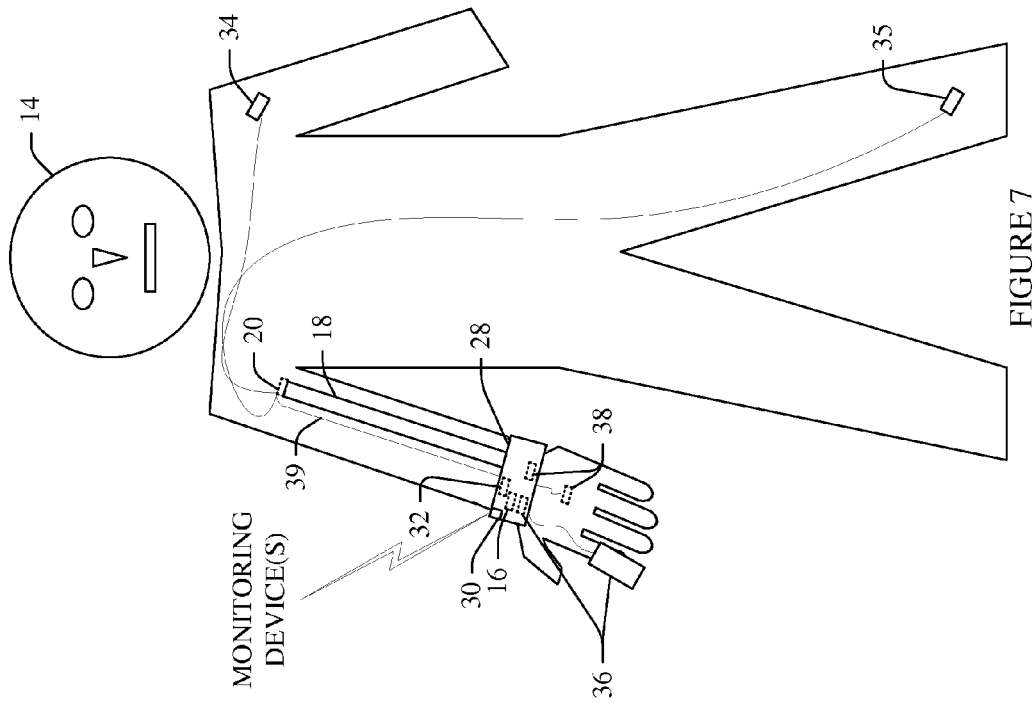
FIG. 7 illustrates another example of the offset pressure measuring device used with a wrist-based monitoring device facilitates measuring multiple physiological parameters.

FIG. 7 illustrates another example of the offset pressure measuring device 18 used with the wrist-based monitoring device 28 that facilitates measuring one or more of: blood pressure, heart electrical activity (ECG), blood oxygen (Sp02), and skin temperature. In this example, the offset pressure sensor 20 is located at an end of the offset pressure measuring device 18 positioned at hear level. As depicted, the offset pressure sensed by the offset pressure measuring device 18 and the heart electrical activity from the heart electrical activity sensors 34 and/or 35 can be routed to the wrist-based monitoring device 28 through common cabling 39. In one instance, the cabling 39 can include separate wires for respective signals, and in another instance, the signals can be combined and concurrently transmitted through the cabling 39 to the wrist-based monitoring device 28 and conveyed to the monitoring device(s) via the transceiver 30. Optionally, a battery pack, the transceiver 30, and other components can be positioned as other areas along the cabling, such as around the upper arms, in a shoulder mounting, or the like.

Figure 8:
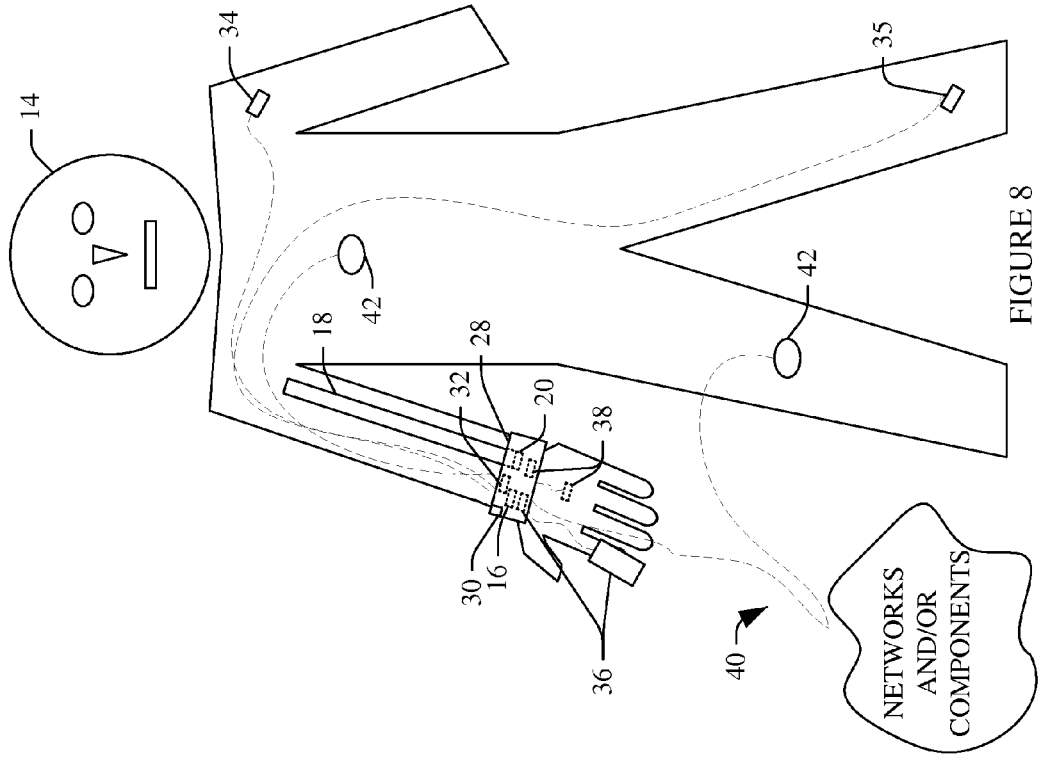
FIG. 8 illustrates an example of the offset pressure measuring device employed within a Wireless Body Area Network (WBAN).

FIG. 8 illustrates an example of the offset pressure measuring device 18 used with the wrist-based monitoring device 28 that at least facilitates measuring blood pressure, heart electrical activity (ECG), blood oxygen (Sp02), and skin temperature in connection with a wireless body area network (WBAN) 40. In this embodiment, at least some of the electrical heart activity sensors 34 and/or 35, the external blood oxygen sensor 36, and the external temperature sensor 38 communicate with the wrist-based monitoring device 28 through wireless technology over the WBAN 40. These signals along with signals (e.g., blood pressure, offset blood pressure, offset-adjusted blood pressure, heart electrical activity, blood oxygen, temperature, etc.) obtained by the wrist-based monitoring device 28 are conveyed by the transceiver 30 to one or more networks and/or components through the WBAN 40. It is to be appreciated that the signals can be independently conveyed and/or variously combined and subsequently conveyed.

The WBAN 40 can include one or more other sensors and/or emitters 42 variously located on the living being 14. For instance, the WBAN 40 can include sensors that capture Electroencephalograms (EEGs), Electromyograms (EMGs), blood pressure acquired from within the ear, pulse, respirations, blood oxygen acquired from within the ear, etc. The one or more emitters can transmit sensed information and/or information such as identity, medication list, scheduled procedures, etc. This information can be conveyed directly to the one or more networks and/or components over the WBAN 40 and/or through the wrist-based monitoring device 28, wherein the wrist-based monitoring device 28 is used as a conduit. Additionally or alternatively, the information is conveyed to the wrist-based monitoring device 28 and conveyed to the one or more networks and/or components through the WBAN 40 via the transceiver 30.

Figure 9:
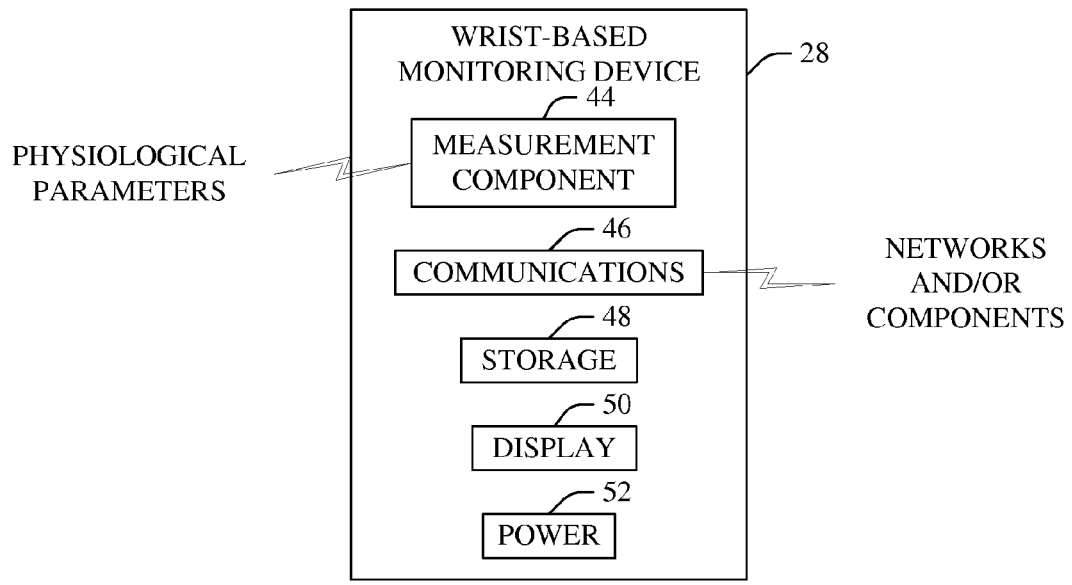
FIG. 9 illustrates an exemplary wrist-based monitoring device.

FIG. 9 illustrates an exemplary wrist-based monitoring device 28. A measurement component 44 is used to sense or receive physiological parameters (e.g., blood pressure, offset-adjusted blood pressure, heart electrical activity, blood oxygen, temperature, etc.) and physiological parameters (e.g., offset pressure, heart electrical activity, blood oxygen, temperature, etc.) sensed by other components and/or other information.

A communication component 46 is used to convey this information to one or more networks and/or components (e.g., a computer, a monitor, a database, etc.). Such conveyance can be through wire and/or wireless technology, including over the WBAN 40 and/or in connection with the transceiver 30. Suitable wireless technologies include, but are not limited to: WTMS; Bluetooth; Zigbee, Embernet, XMAX, WiMAX, WiFi, cellular, Personal Communications Service (PCS); 802.11x; 802.15.x, 802.3x, 802.16x, etc.

A storage component 48 is used to store physiological parameters, algorithms for processing the physiological parameters, software applications, and/or firmware. The storage component 48 can include various types of storage media such as Random Access Memory (RAM), Read Only Memory (ROM such as PROM, EPROM and EEPROM), portable flash memory, etc.

A display component 50 provides a mechanism for presenting physiological parameters to a user. The display component 50 can include light emitting diodes and seven segment displays as well as other elements that visually and/or audibly present information.

A power component 52 powers the various other components of the wrist-based monitoring device 28. The power component 52 can include a converter for converting AC power from a receptacle to suitable DC power. The power component 52 can also include a battery (e.g., non-rechargeable or rechargeable, including lead-acid, Lithium ion (Li), Nickel metal hydride (NiMH), Nickel-Cadmium (NiCd), which can be internal to the wrist-based monitoring device 28 and an external portable battery.

It is to be appreciated that the wrist-based monitoring device 28 can be portable and mobile, which allows an individual to move around. The portability can also be leveraged to mitigate the numerous cables associated with individual monitoring sensors and devices. Furthermore, continuous or quasi-continuous monitoring can be performed without any need of a clinician. In some instance, wrist-based monitoring device 28 can be the medical information system's primary contact with the patient, allowing bi-directional communications and monitoring various aspects of the patient's interactions with the medical system.

Figure 10:
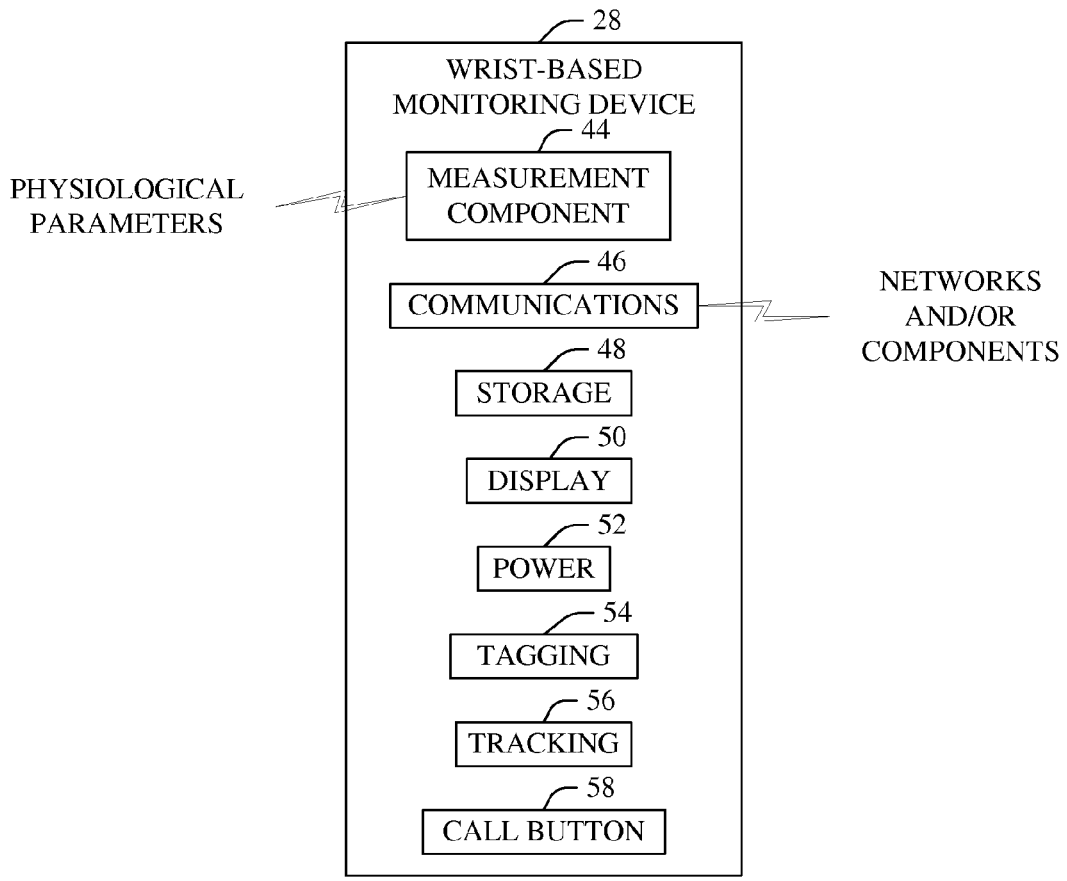
FIG. 10 illustrates another exemplary wrist-based monitoring device.

In FIG. 10, the wrist-based monitoring device 28 further includes a tagging component 54 and a tracking component 56. The tagging component 54 is used to store information about the device 28 such as model number, software release, firmware version, last calibration date, etc., and/or information about the entity monitored such as identification, etc. This information can be retrieved, modified, and/or removed through suitable devices by authorized personnel.

The tagging component 54 can include various technologies that facilitate such capabilities. For instance, the tagging component 54 can include one or more radio frequency identification (RFID) tags that periodically emit information and/or emit information upon request (e.g., when entering a magnetic field, from an RFID tag writer/reader, on entering or leaving a room, etc.). Active and/or passive RFID tags can be used. In another instance, the tagging component 54 can include a bar code (e.g., similar to a Universal Product Code (UPC), an Electronic Product Code (EPC), and the like), which can be scanned or otherwise read. The information stored within the tagging component 54 can be presented on the display component 50 or accessed by a PDA, computer, etc.

The tracking component 56 is used to track the wrist-based monitoring device 28. The tracking component 56 can include various componentry that facilitates local and extended area tracking. For instance, the tracking component 56 can include transmitters with particular frequencies, encoding schemes, compression schemes, keys, etc. for communicating with and/or operating within one or more particular networks. In another instance, the tracking component 56 can include Global Positioning System (GPS) componentry, which uses satellite technology for determining the location of the wrist-based monitoring device 28 from essentially anywhere on the Earth. The information stored within and obtained from the tagging component 54 can also be used to track the wrist-based monitoring device 28.

A call button 58 provides a mechanism in which a user of the device can submit a request for assistance. This request can include audible and/or visual notifications, and can work in connection with existing call features used by a facility. For instance, the call button 58 can work in conjunction with a bedside "nurse call" button.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A physiological measurement system comprising:
   a wrist mounted unit configured to be mounted to a wrist of a patient;
   a blood pressure sensor that measures a blood pressure relative to atmospheric pressure at the wrist, the blood pressure sensor being carried by the wrist mounted unit to abut the wrist;
   a pressure compensation system that determines an offset pressure between the wrist and a heart level, the pressure compensation system including:
      a pressure sensor that senses pressure in a fluid filled cavity that extends from a level of the blood pressure sensor to the heart level relative to atmospheric pressure; and
      a component which combines the blood pressure measured relative to atmospheric pressure and the cavity fluid pressure relative to atmosphere to generate a measure of blood pressure at the heart level;
   a plurality of physiological parameter sensors configured to be mounted to the patient, each sensor sending sensed physiological parameters over a wireless body area network;
   a transceiver mounted in the wrist mounted unit and coupled to the wireless body area network to at least receive the sensed physiological parameters;
   a communication component mounted in the wrist mounted unit and connected with the transceiver and the pressure sensor to receive the sensed physiological parameters and the blood pressure at heart level therefrom, the communication component wirelessly transmitting the sensed physiological parameters and the blood pressure at heart level from the wrist mounted unit to a remote medical network.

2. The system as set forth in claim 1, the pressure sensor being disposed in contact with the fluid in the cavity, to measure a pressure within the cavity relative to atmospheric pressure.

3. The system as set forth in claim 2, wherein the pressure sensor is disposed at an end of the cavity that is positioned at one of:
- about the heart level, and
- about blood pressure sensor level.

4. The system as set forth in claim 1, wherein the pressure sensor includes a solid state transducer, an amplifier, and an analog-to-digital converter which converts the heart level blood pressure to a digital blood pressure value.

5. The system as set forth in claim 1, wherein the fluid filled cavity includes a flexible tube.

6. The system as set forth in claim 1, further including:
- a call button attached to the wrist mounted unit and connected with the communication unit for transmitting a call for assistance to the medical network.

7. The system as set forth in claim 1, further including:
- a tracking unit disposed in the wrist mounted unit and connected with the communications unit which communicates patient location to the medical network.

8. The system as set forth in claim 1, further including:
- a component connected with the wrist unit which generates an electrical signal identifying the monitored patient.

9. A physiological measurement system comprising:
- a wrist unit which extends around a patient's wrist;
- a blood pressure sensor mounted to the wrist unit;
- a fluid filled tube that extends from the wrist unit to a level of the heart;
- a pressure sensor that measures a pressure of fluid in the tube;
- a monitoring component that combines the measured blood pressure and the fluid pressure measured in the tube to render a heart level blood pressure signal;
- a plurality of ECG electrodes;
- ECG leads that run from the wrist unit along and exterior to the fluid filled tube and to the ECG electrodes to connect the ECG electrodes to the wrist unit;
- a blood oxygen sensor connected with the wrist unit to convey blood oxygen signals thereto;
- at least one analog to digital converter which digitizes the heart level blood pressure signals, the ECG signals, and the blood oxygen signals, the analog to digital converter being disposed in the wrist unit;
- a computer memory which stores the digital heart level blood pressure signals, the digital ECG signals and the digital blood oxygen signals, the computer memory being disposed in the wrist unit;
- a communication component which converts the stored digital heart level blood pressure signals, the stored digital ECG signals and the stored digital blood oxygen signals to RF signals and transmits the RF signals wirelessly to a medical network; and
- a battery which powers the at least one analog to digital converter, the computer memory, and the communication component, the battery being disposed in the wrist unit.

10. The system as set forth in claim 9, further including:
- a call button attached to the wrist unit and connected with the communication unit by which the patient can submit a call for assistance to the medical network.

11. The system as set forth in claim 10, further including:
- a tracking unit disposed in the wrist unit for tracking a location of the wrist unit, the tracking unit being connected with the communications unit which communicates the location of the wrist unit to the medical network.

12. The system as set forth in claim 10, further including:
- a tracking component connected with the wrist unit which identifies the monitored patient.

13. The system as set forth in claim 12, wherein the tracking component includes a RFID tag.

14. The system as set forth in claim 12, wherein the tracking component includes a bar code.

* * * * *